United States Patent [19]

van de Waart et al.

[11] Patent Number: 5,308,756
[45] Date of Patent: May 3, 1994

[54] PROTEIN S CHROMOGENIC ASSAY

[75] Inventors: Piet van de Waart, Wünnewil; Barry J. Woodhams, Fribourg, both of Switzerland

[73] Assignee: Baxter Diagnostics Inc., Deerfield, Ill.

[21] Appl. No.: 796,032

[22] Filed: Nov. 20, 1991

[51] Int. Cl.$^5$ .................... C12Q 1/56; G01N 33/86
[52] U.S. Cl. ........................ 435/13; 435/71; 435/74; 435/69.6; 435/69.2; 435/810; 435/962; 435/975; 436/69; 436/86; 530/413
[58] Field of Search ............... 435/13, 810, 69.2, 69.6, 435/962, 74, 71, 975; 436/69, 86, 808; 530/380, 387, 413

[56] References Cited

U.S. PATENT DOCUMENTS

| | | | |
|---|---|---|---|
| 4,480,030 | 10/1984 | Svendsen | 435/13 |
| 5,001,069 | 3/1991 | Bartl et al. | 435/13 |
| 5,147,805 | 9/1992 | Preda et al. | 436/86 |

FOREIGN PATENT DOCUMENTS

| | | | |
|---|---|---|---|
| 260707 | 3/1988 | European Pat. Off. | |
| 406971 | 9/1991 | European Pat. Off. | 435/13 |
| WO9101382 | 4/1990 | PCT Int'l Appl. | 435/13 |

OTHER PUBLICATIONS

Thrombosis Research 63(1) 189-193 (1991).
Bertina, R. M. "Specificity of Protein C and Protein S Assays"; Res. Clin. Lab.; 20, 127-138 (1990).
High, K. A.; "Antithrombin III, Protein C, and Protein S" Arch. Pathol. Lab. Medicine; 112 (Jan.), 28-36 (1988).
Kobayashi, I. et al.; "Functional Activity of Protein S determined with Use of Protein C Activated by Venom Activator"; Clinical Chemistry; 35 8, 1644-1648 (1989).
Koedam, J. A. et al., "Inactivation of human factor VIII by Activated Protein C" J. Clinical Investigation; 82 4, 1236-1243 (1988).
Preda, L. et al.; "A Prothrombin Time-Based Functional Assay of Protein S"; Thrombosis Research; 60, 19-32 (1990).
Rick, M. E. et al.; "Factor IXa and von Willebrand factor modify the inactivation of factor VIII by activated protein C"; J. Lab Clin. Med. 115 4, 415-421, (1990).
Suzuki, K and Nishioda, J.; "Plasma Protein S Activity Measured Using Protac, a Snake Venom Derived activator of Protein C"; Thrombosis Research; 49 2, 241=251, (1988).
van der Waart, P. et al; "A Functional Test for Protein S Activity in Plasma" Thrombosis Research; 48, 427-437 (1987).

*Primary Examiner*—Johnnie R. Brown
*Assistant Examiner*—A. Varma
*Attorney, Agent, or Firm*—Louise S. Pearson; Michael P. Bucklo; Cynthia G. Tymeson

[57] ABSTRACT

A chromogenic assay for determination of Protein S, using an indicator of Factor Xa as a measure of Protein S concentration. This technique utilizes the dependency of activated Protein C on Protein S in order to inactivate a known portion of Factor VIII. Residual Factor VIII is then activated and acts with Factor IXa to activate Factor X. The chromogenic substrate is then cleaved by Factor Xa and the rate of conversion of the indicator molecule is an indirect indicator of free Protein S.

29 Claims, No Drawings

PROTEIN S CHROMOGENIC ASSAY

FIELD OF THE INVENTION

This invention relates generally to the field of chromogenic assays and more specifically to chromogenic assays for the determination of levels of Protein S contained in plasma and other fluids.

BACKGROUND OF THE INVENTION

The blood coagulation cascade or system is comprised of a group of zymogens that are converted by limited proteolysis to active enzymes. This active cascade of enzymes ultimately forms a fibrin clot from fibrinogen. This blood clotting cascade is divided into two pathways, extrinsic and intrinsic. The series of reactions that convert the zymogens to enzymes requires a variety of protein cofactors such as Blood Factors VIII and V. In turn these cofactors are regulated by a number of other proteins such as Protein S and Protein C. High, K.A., *Antithrombin III, Protein C, and Protein S,* Arch. Pathol. Lab. Med. (1988); Vol. 112:pp.28-36.

Protein S is a naturally occurring anticoagulant protein. It circulates in two forms—free and bound to C4B. Approximately 40% of the protein is found in the free form while 60% exists in the bound form. Only the free form has functional activity. Blanc, P., et al., *Deficit Constitution en Proteine S a l'Origine de Thrombose Vasculaire Digestive,* La Presse Medical (1990): Vol. 19: pp.416-419. Protein C is also an anticoagulant.

Protein S and Protein C exert their effect on the intrinsic pathway of the clotting cascade system. Protein S does not require activation by another factor, however, it is active only in the presence of activated Protein C which is activated by thrombin (Factor IIa). Activated Protein C acts as an anticoagulant by inactivating Factor V and VIII. Protein S increases the anticoagulatory effect of Protein C.

Von Willebrand Factor decreases the inactivation of Factor VIII by activated Protein C and Protein S and that effect is enhanced by the active site of Factor IXa. The von Willebrand Factor acts by binding Factor VIII, thereby protecting it from inactivation. Rick, M.E., *Factor IXa and von Willebrand Factor Modify the Inactivation of Factor VIII by Activated Protein C,* Journal Lab. Clin. Med. (1990); Vol. 115(4): pp. 415-421.

Deficiency of Protein S has been associated with a number of disease states. For example, individuals who have reduced Protein S levels have an increased risk of venous thromboembolism. In fact, Protein S deficiency is responsible for 8-10% of the cases of venous thromboembolism occurring in young people. Preda, L. et al., *A Prothrombin Time-Based Functional Assay of Protein S,* Thrombosis Research (1990); Vol. 60:pp.19-32.

There are two types of Protein S deficiency. The first type is associated with mildly reduced levels of total Protein S, but markedly reduced levels of free Protein S, while the second type of Protein S deficiency has markedly reduced levels of both free and total Protein S Woodhams, B.J., et al., *Functional Protein S Assay Shows Improved Correlation with Clinical Symptoms in Hereditary Deficiency,* Thrombosis Research (1990); Vol. 57:pp.651-657. The only known treatment for Protein S deficiency is lifelong therapy with sodium warfarin. High, K.A., *Antithrombin III, Protein C, and Protein S,* Arch. Pathol. Lab. Med. 1988; 112:pp.28-36.

There are a number of methods available to measure Protein S levels in individuals. These methods can be divided into two classes. The first class, Protein S antigen level assays, measures both free and bound (total) Protein S. The second class, functional Protein S assays, measures only free Protein S since only free Protein S has any functional activity.

In the antigen level assays, Protein S levels (total Protein S) are measured using a variety of techniques including: ELISA, RIA, IRMA, and electroimmunodiffusion (Laurell Rocket Technique). All of these techniques use polyclonal antibodies to the antigen. One difficulty associated with these methods, however, is that the relative affinities of the antibodies to the free and bound Protein S must be known in order to determine the actual concentration of functional Protein S. Therefore, antigen level assays are of limited value since they cannot unequivocally distinguish the functionally active or free form of Protein S from the bound form which is not functionally active. Bertina, R., *Specificity of Protein C and Protein S Assays,* Res. Clin. Lab. (1990); Vol. 20:pp127 at 132-134. Moreover, this measurement of the total Protein S antigen does not distinguish between the the two types of Protein S deficiencies. Furthermore, antigen level assays require high sample dilutions and long incubation times.

Alternatively in the functional Protein S assays, functional or free Protein S activity levels are measured using clotting times or thromboplastin times. One functional Protein S assay is based on a prolongation of Factor Xa initiated clotting times. In this assay, Protein S which requires activated Protein C, acts as a co-factor for the activated Protein C to inactivate Factor Va which therefore prolongs clotting times. Some of the other functional Protein S assays activate the Protein C using a snake venom activator. Another functional Protein S assay is based on the activated partial thromboplastin time (APTT). This method is based on the need for functional Protein S to act as a co-factor for the activated Protein C dependent inhibition of blood coagulation. A primary problem associated with this type of test is its inapplicability to patients who are receiving anti-coagulants such as heparin. Since most patients requiring Protein S tests are using oral anticoagulants at the time of the sample collection, these types of tests cannot be used accurately. Bertina, R., *Specificity of Protein C and Protein S Assays,* Res. Clin. Lab.; 20:p.127. Another problem associated with the APTT type assay is that it relies upon the presumption that normal plasma will give a 100% correction in thromboplastin time. It has been recognized that there is a dependence of prolongation of clotting times on activated Protein C concentration. Thus, persons performing the assay must construct a full standard curve each time the assay is run. Moreover, the assay is very costly and a long time is needed for measurement, while the coagulation time may only be extended by 10 seconds. These factors leave room for error and reduce lab efficiency.

To solve many of the above problems, we have created a test using chromogenic substrates to measure activity levels of functional Protein S. Chromogenic substrates have previously been used in the determination of Factor VIII levels. These Factor VIII assays recognize that Factor Xa concentrations can be linked to Factor VIIIa concentrations by exploiting the coagulation cascade system (Dade ® Factor VIII Chromogenic Assay: Baxter Diagnostics Inc.). Protein C concentrations also have been determined with chromogenic substrates which are cleaved by activated Protein C making a direct and simple measurement for Protein C. High, K.A., *Antithrombin III, Protein C, and Protein S,* Arch. Pathol. Lab. Med. (1988); Vol. 112:pp.28-36. Since Protein S is not an enzyme, however, it cannot be measured directly using chromogenic substrates. Thus, this invention exploits the relationship of Protein S with other blood coagulation proteins.

The method of the present invention provides an assay which quantitatively determines only the functional levels of Protein S and does not utilize expensive antibody technology to determine the Protein S concentration. This method has an advantage over other Protein S assays in that this assay does not have the problems associated with arbitrarily designating normal pools as having a clotting of 100% and basing other samples on that normal pool value. This is especially true since pregnancy lowers the free Protein S activity. Suzuki, K. et al., *Plasma Protein S Activity Measured Using Protac, A Snake Venom Derived Activator of Protein C,* Thrombosis Research (1988); Vol. 49:pp.241-251. including a sample from a pregnant woman into the pool would obviously lower the final pool value and distort results.

This invention provides a highly sensitive, reproducible, and convenient assay for determination of the levels of Protein S contained in blood serum, plasma, and other fluids. The invention recognizes that the effect of von Willebrands factors must be eliminated to obtain accurate and reproducible results. Again, since Protein S is not an enzyme, its functional concentration cannot be measured directly by way of a chromogenic substrate. Instead, the ability of Protein S to enhance the inactivation of Factor VIII by activated Protein C is exploited. Residual Factor VIII is activated and then acts wi&:h Factor IXa to activate Factor X. An indicator such as a chromogenic substrate to Factor Xa is then converted by Factor Xa to a measurable signal molecule. The signal molecule can then be related to the amount of Protein S in the sample.

SUMMARY OF THE INVENTION

In this invention, a sample of blood serum, plasma or other Protein S-containing fluid is incubated with a reagent capable of eliminating the effects of any von Willebrand factor and a solution of activated Protein C (APC), phospholipid and calcium ions (in the most preferred embodiment, the calcium is present as calcium chloride). This Protein S-containing solution is then incubated for a period of time sufficient to eliminate the effect of the von Willebrands factor. Thereafter, an appropriate dilution of this Protein S-containing solution is mixed with Factor VIII, of either natural or recombinant origin. The concentration of Protein S in the mixture correlates directly to the amount of Factor VIII that is inactivated. Residual Factor VIII activity is measured by the addition of Factor IXa, Factor IIa, Factor X from natural or recombinant sources and calcium ions as follows: the residual Factor VIII is activated by Factor IIa; the activated Factor VIII and Factor IXa acitvate Factor X to Factor Xa; an indicator agent or substrate specific for Factor Xa is added to the reaction mixture; the indicator agent reacts with the Factor Xa so formed, to release a signal molecule, which may be measured spectrophotometrically.

In accordance with the method of this invention, an assay is provided which has a high degree of sensitivity and reproducibility for functional Protein S concentration. A further object of this invention is to provide an assay for Protein S which is not affected by the presence of heparin and other blood clot interactive substances. Another object of this invention is to provide a kit for the convenient performance of routine laboratory assays of Protein S containing fluids. A further object of this invention is to provide a bulk source of assay components to facilitate the operation of automated equipment capable of processing for assaying large numbers of test samples.

The advantages and performance of the present invention will be better understood by reference to the following detailed description and Examples.

DETAILED DESCRIPTION OF THE PREFERRED EMBODIMENT

The method of the assay of the present invention comprises the steps of:

Combining into a mixture a bodily fluid sample or control containing Protein S with a reagent to eliminate the effects of von Willebrands factor, as more fully described below, and activated Protein C in the presence of phospholipids and calcium ions ($Ca^{++}$) in an amount sufficient to inactivate a portion of a predetermined amount of Factor VIII. The reagent which is used to eliminate the effects of von Willebrands factor should be present in an amount sufficient to inactivate substantially all of the von Willebrands factor present in the sample. The activated Protein C (as a starting concentration) in the preferred embodiment should be in the range from about 0.5 nM to about 50 nM, and most preferably about 2 nM to about 20 nM. The calcium ion concentration (as a starting reagent) in the preferred embodiment should be in the range from about M to about 20 mM, and most preferably about 5 mM to about 15 mM. During the Factor VIII inactivation the final calcium ion concentration is most preferable from about 1 to about 5 mM.

2. Incubating the mixture for a time sufficient to eliminate the von Willebrands factor interaction with Factor VIII. In the preferred embodiment the incubation time should be in the range from about 0.1 minute to about 5 minutes, and most preferably about 0.5 minute to about 2 minutes.

3. Combining the incubation mixture with a known amount of Factor VIII. In the preferred embodiment the Factor VIII (as a starting reagent) should preferably be in the range from about 0.01 u/mL to about 1 u/mL, and most preferably from about 0.1 u/mL to about 0.3 u/mL.

4. Incubating the mixture for a time sufficient to inactivate a portion of the Factor VIII. The preferred time should be in the range from about 1 minute to about 15 minutes, and most preferably about 3 minutes to about 8 minutes.

5. Combining Factor IXa, phospholipids, Factor X and Factor IIa and calcium ion with the incubation mixture whereby there are sufficient amounts of Factor IIa and calcium ion to activate the remaining Factor VIII, and sufficient amounts of Factor IXa, phospholipids and calcium to activate the Factor X. The Factor IXa (as a starting reagent) should preferably be in the range from about 10 nM to about 1000 nM, and most preferably about 100 nM to about 300 nM. The Factor X (as a starting reagent) should preferably be in the range from about 50 nM to about 3000 nM, and most preferably from about 300 nM to about 1000 nM. The Factor IIa (as a starting reagent) should preferably be in the range from about 1 nM to about 200 nM, and most preferably about 20 nM to about 100 nM.

6. Incubating the mixture for a time sufficient to convert all or a portion of the Factor X to Factor Xa. The preferred time should be in the range from about 0.2 minutes to about 10 minutes, and most preferably from about 1 minute to about 3 minutes.

7. Adding a sufficient amount of thrombin inhibitor to inhibit thrombin activity without affecting Factor Xa activity, adding, either at the same time or following the addition of the thrombin inhibitor, an indicator agent, as more fully described below, capable of reacting with Factor Xa, to release a signal molecule, the quantity of indicator agent being sufficient to generate a signal molecule in amounts that can be detected. The thrombin inhibitor (as a starting reagent) should preferably be in the range from about 1 μM to about 500 μM, and most preferably in the range from about 10 μM about 50 μM. The indicator agent (as a starting reagent) should preferably be in the range from about 0.1 mM to about 5 mM, and most preferably from about 0.2 mM to about 1 mM.

8. Measuring the signal molecule.

Final concentrations of signal molecule can be conveniently determined by reference to the examples herein and by other standard techniques.

The foregoing method may be exemplified by reference to the following equations:

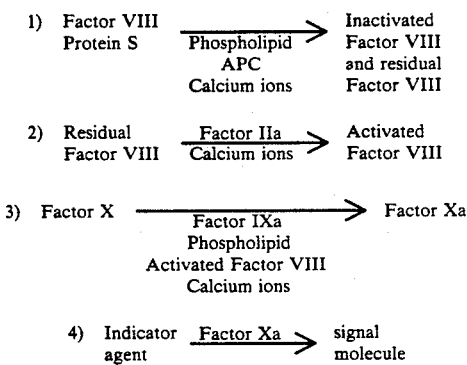

In practicing the method of the present invention the reagents can be added in any order consistent with the above mentioned equations. Additionally, Factors IIa, VIII, IXa, and X can be obtained from virtually any animal or human source and can be prepared by any fractionation or concentration method known to the art. For example, see Methods of Enzymology 80 (1981), Academic Press Inc. A highly purified source of such factors is from recombinant vectors propagated in suitable host cell lines. Lin S.W. et al., J. Biol. Chem. (1990) Vol. 265(1):pp.144-150. One advantage to using factors from animal or recombinant vector sources is the assurance that the product factors will not be contaminated with human pathogens such as hepatitis A and B, HTLV-III or other such viruses. In the preferred embodiment of the present method, blood coagulation factors are of bovine origin.

For the purpose of this invention, it is necessary to remove or eliminate the effects of substances which interfere with the Protein S activity assay. Thus, because von Willebrands Factor binds Factor VIII and decreases its inactivation by activated Protein C and Protein S and because the inactivation of Factor VIII is directly proportional to the amount of functional free Protein S in the sample, a reagent must be added to eliminate the von Willebrands Factor binding to Factor VIII. Such reagents include but are not limited to anti-von Willebrands antibody, inactivated Factor VIII, any fragments of Factor VIII which bind to von Willebrands Factors, synthetic peptides which bind to von Willebrands Factors or specific enzymes (eg. snake venom enzymes). The amount of reagent used to eliminate the effects of the von Willebrands Factor should preferably be in the range of from about 10 nM to about 2000 nM, and most preferably from about 100 nM to about 1000 nM. Recently a mutant Factor VIII has been prepared which does not bind with von Willebrand Factor. Leyte, A. et al., *Sulfation of $Tyr^{1680}$ of Human Blood Coagulation Factor VIII is Essential for the Interaction of Factor VIII with von Willebrand Factor*, J. Biol. Chem. (1991); 266 (2):pp.740-746. This Factor VIII can be substituted in the procedure and the step of eliminating the von Willebrands Factor would not be required.

The conversion of Factor X to Xa and the inactivation of Factor VIII by activated Protein C and Protein S, proceeds most efficiently in the presence of lipids and phospholipids. U.S. Pat. Nos. 4,666,831 and 4,698,299 describe the use of certain phospholipids in diagnostic assays. The lipids and phospholipids of this invention include but are not limited to such representative compounds disclosed in those patents such as phosphatidyl choline, phosphatidyl serine, or cholesterol and mixtures thereof in various proportions. Other lipid and phospholipid compositions can be substituted as well, the ranges of acceptable composition are 5 to 40 mole-% of phosphatidyl serine, 1 to 20 mole-% cholesterol, and 50 to 90 mole-% of phosphatidyl choline.

Any chemical source of calcium ion can be used to effectuate the conversion of Factors VIII and X. Sufficient calcium ions can be added to the original incubation mixture to drive the reaction converting Factor VIII to activated and inactivated Factor VIII and Factor X to Factor Xa or a lesser amount can be added to the original incubation mixture with a second amount of calcium ion to be added at the time Factor X is to be converted. While the source of calcium cation (Ca++) include but are not limited to $CaCl_2$, $Ca(NO_2)_2$, $CaSO_4$, or other inorganic or organic calcium cation containing compounds, the preferred source is $CaCl_2$.

The indicator agent of the present invention is a molecule capable of reacting with blood coagulation Factor Xa. In such reactions, by-products of chemical reactions must be generated which produce a measurable signal moiety; U.S. Pat. Nos. 4,440,678; 4,480,030; 4,568,636 and 4,622,389 describe classes of chromogenic compounds capable of reacting with Factor Xa. The indicator agents of this invention include but are not limited to such representative compounds as disclosed in those patents. The indicator agent must react with Factor Xa to yield a signal molecule which can be measured (eg., visually or photometrically such as by fluorescence) and correlated to the concentration of Factor Xa. The most preferred member of this class of indicator compounds reacts with Factor Xa according to the following equation:

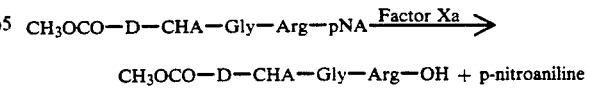

$CH_3OCO-D-CHA-Gly-Arg-OH$ + p-nitroaniline wherein D represents the dextrorotary stereoisomer, CHA is cyclohexylanine, Gly is glycine, Arg is arginine and pNA is paranitroaniline. Upon reaction with Factor Xa, a signal molecule p-nitroaniline is released, which can be conveniently measured by spectrophotometric determination using either a rate or end-point analysis at 405 nanometers.

Other indicator agents which are applicable with the present invention are available also. From the preceding disclosure it will be apparent to those skilled in the art that the signal moiety of the target indicator agent can be radiolabelled, preferably by tritium or carbon 14, and the signal molecule upon release can be isolated as by gel exclusion chromatography, dialysis, immunoadsorption, or other convenient separation techniques.

A thrombin inhibitor is used to block thrombin activity on chromogenic substrate for Factor Xa. Useful thrombin inhibitors include but are not limited to N-alpha (2-Naphthylsulfonylglycyl)-D,L-Amidinophenylalanine piperidide (alpha NAPAP) and hirudin. In the preferred embodiment the thrombin inhibitor, alpha NAPAP, is included in with the indicator composition. The alpha NAPAP is preferably in the range from about 10 nM to about 5000 nM and the most preferably in the range from about 500 nM to about 2000 nM.

An optional step in the present assay consists of adding a quenching agent to the incubation mixture at a fixed point in time after commencement of the reaction converting Factor X to Factor Xa. This time ranges from about 0 to 60 and most preferably from 0 to 20. The quenching composition of the preferred embodiment is a buffer composition containing a chelator which binds calcium ions. Typical chelators are EDTA or EGTH. The quenching composition of the preferred composition is a buffered solution comprised of Tris, ethylenediamine tetraacetic acid (EDTA), sodium chloride, and sodium azide. Alternatively and in the preferred embodiment, the EDTA is included in with the indicator composition. The EDTA should preferably be in the range from about 2 mM to 100 mM, and most preferably in the range from 10 mM to 20 mM. The sodium chloride should be in the range from 10 mM to 1000 mM, and most preferably in the range from 100 mM to 400 mM, however, the NaCl is not critical.

Additionally instead of measuring the rate of appearance of p-nitroaniline at 405 nm or any other measurable product, an end-point analysis can be performed by adding acids such as citric acid or acetic acid at a fixed point in time after the addition of the indicator agent and then reading the absorbance at 405 nm or the appropriate wavelength. This time ranges from about 0 to 5 minutes and most preferably from about 0 to 1 minute.

Another optional step would be to use native Protein C instead of activated protein C and to activate the Protein C using snake venom activator or other Protein C activators. This method would require an additional step of adding the Protein C activator and incubating for a time sufficient to activate the Protein C.

It is contemplated within the scope of the present invention that the components of the Protein S assay can be available as a kit for the convenient and routine performance of a large number of such assays. The concentrations of the components as starting materials have been indicated above. The assay kit comprises: a first vessel containing a sufficient amount of reagent to eliminate the effects of von Willebrands factor in the samples, and a sufficient amount of activated Protein C which in the preferred embodiment is from human source, to inactivate a portion of a predetermined amount of Factor VIII and sufficient amounts of phospholipid and calcium ion to facilitate the inactivation of the Factor VIII; a second vessel containing a fixed and known amount of Factor VIII; a third vessel containing a sufficient amount of Factor IIa and calcium ion to activate the remaining Factor VIII, and sufficient amounts of Factor X and Factor IXa so as to activate the Factor X to Factor Xa in the presence of the activated Factor VIII; a fourth vessel containing a sufficient quantity of an indicator agent capable of reacting with Factor Xa, the quantity of indicator agent being sufficient to produce a measurable signal and a sufficient amount of a thrombin inhibitor to inhibit thrombin activity without affecting Factor Xa activity; and optionally a fifth vessel containing sufficient quantity of a quenching agent to stop the conversion of Factor X to Factor Xa. Alternatively and in the preferred embodiment, the quenching agent is an additional component of the fourth vessel. The quantities are sufficient to perform one or a plurality of Protein S assays.

In performing the assay of this invention, great variations in protein concentration, incubation times, reagent concentrations, and temperatures can be employed. The selection of particular assay parameters will be influenced by the source, type and size of the sample to be assayed, the anticipated levels of Protein S contained therein, and the threshold of sensitivity desired. Taking these circumstance into account, selection of assay parameters will be apparent to those skilled in the art. The parameters of the assay, which will enable anyone skilled in the art to carry out the assay in accordance with preferred embodiments are set forth in the Examples which follow.

EXAMPLE 1

Microtitre plates were prepared by adding 25 ul of sample, 25 ul of a 0.016M tris-(hydroxymethyl)aminomethane (Tris) buffer at pH 8.0, 25 ul of a starting reagent to each well. The starting reagent was comprised of a water reconstituted lyophilized preparation containing 30 nM activated human Protein C, 30 uM phospholipid, 15 n M activated human Protein C, 30 uM phospholipid, 15 nM calcium chloride, 1.4 uM anti von Willebrands factor, 0.016 M Tris buffer at ph 8, 0.5% polyethylene glycol (PEG) 6000, i% BSA (Bovine Serum Albumin) and 125 mM NaCl. The plates were incubated for 2 minutes at 37° C. to eliminate the effects of the von Willebrands factor. After incubation a 25 ul of a support reagent was added to each well. The support reagent was comprised of a water reconstituted lyophilized preparation containing bovine Factor VIII of at 0.2 units/mL and 0.016 M Tris buffer at pH 8, 0.5% PEG 6000, 1% BSA and 125 mM NaCl and 1.0 mM calcium chloride. The plates were then incubated for 5 minutes at 37° C.. The incubation was followed by addition of 25 ul of a mediator reagent. The mediator reagent was comprised of a water reconstituted lyophilized preparation containing approximately 300 nM bovine Factor IXa, 0.5 uM bovine Factor X, 100 nM bovine Factor IIa and 10 nM (2[N-morpholino]ethane sulfonic acid) (MES) buffer at pH 5.6, 0.5% PEG 6000, 1% BSA, and 125 mM NaCl. The plates were then incubated for 1 minute at 37° C. This incubation was followed by an addition of 100 ul of substrate reagent. The substrate reagent was comprised of a water reconstituted lyophilized preparation containing approximately 0.4 mM CH3O-CO-D-CHA-Gly-Arg-pNA, N alpha (2-naphthylsulfonylglycyl) -D-L-Amidinophenyl alaninepiperidide (alpha NAPAP) which is a thrombin inhibitor, 15 mM EDTA, 0.250 M NaCl and 0.020 M Tris at pH 8. The plates were then incubated for 1 minute at 37° C.. This incubation was followed by addition of 50 ul of 1 M citric acid and the spectrophotometric absorbance was obtained at 405 nm using a spectrophotometer.

EXAMPLE 2

Semi-micro cuvettes were prepared by adding 50 ul of sample, 50 ul of a 0.016 M tris-(hydroxymethyl)aminomethane (Tris) buffer at pH 8.0, 50 ul of a starting reagent to each well. The starting reagent was comprised of a water reconstituted lyophilized preparation containing 30 nM activated human Protein C, 30 uM phospholipid, 15 mM calcium chloride, 1.4 uM anti von Willebrands factor, .016 M Tris buffer at pH 8, 0.5% polyethylene glycol (PEG) 6000, 1% (Bovine Serum Albumin) BSA and 125 mM NaCl. The cuvettes were incubated for 2 minutes at 37° C. to eliminate the effects of the von Willebrands factor. After incubation a 50 ul of a support reagent was added to each well. The support reagent was comprised of a water reconstituted lyophilized preparation containing bovine Factor VIII of at 0.2 units/mL and 0.016 M Tris buffer at pH 8, 0.5% PEG 6000, 1% BSA and 125 mM NaCl and 1.0 mM calcium chloride. The cuvettes were then incubated for 5 minutes at 37° C.. The incubation was followed by addition of 50 ul of a mediator reagent. The mediator reagent was comprised of a water reconstituted lyophilized preparation containing approximately 300 nM bovine Factor IXa, .5 uM bovine Factor X, 100 nM bovine Factor IIa and 10 nM MES buffer at pH 5.6, .5% PEG 6000, 1% BSA, and 125 mM NaCl. The cuvettes were then incubated for 1 minute at 37° C.. This incubation was followed by an addition of 200 ul of substrate reagent. The substrate reagent was comprised of a water reconstituted lyophilized preparation containing approximately 0.4 mM CH3O-CO-D-CHA-Gly-Arg-pNA, N alpha (2-naphthylsulfonylglycyl) -D-L-Amidinophenyl alanine-piperidide (alpha NAPAP) which is a thrombin inhibitor, 15 mM EDTA, 0.250 M and 0.020 M Tris at pH 8. A kinetic determination of the reaction in the cuvette was performed immediately after addition of the substrate by recording the change in optical density at 405 nm for one minute.

EXAMPLE 3

Semi-micro cuvettes are prepared by adding 50 ul of sample, 50 ul of a .016 M tris-(hydroxymethyl)aminomethane (Tris) buffer at pH 8.0, 50 ul of a starting reagent to each well. The starting reagent is comprised of a water reconstituted lyophilized preparation containing 30 nM human Protein C, 30 uM phospholipid, 15 mM calcium chloride, 1.4 uM anti-von Willebrands factor, 0.016 M Tris buffer at pH 8, 0.5% polyethylene glycol (PEG) 6000, 1% BSA and 125 mM NaCl. The cuvettes are incubated for 2 minutes at 37° C. to eliminate the effects of the von Willebrands factor. Snake venom activator is added to the cuvettes in an amount sufficient to activate the Protein C. After incubation a 50 ul of a support reagent is added to each well. The support reagent is comprised of a water reconstituted lyophilized preparation containing bovine Factor VIII at 0.2 units/mL and 0.016 M Tris buffer at pH 8, 0.5% PEG 6000, 1% BSA and 125 mM NaCl and 1 mM calcium chloride. The cuvettes are then incubated for 5 minutes at 37° C.. The incubation is followed by addition of 50 ul of a mediator reagent. The mediator reagent is comprised of a water reconstituted lyophilized preparation containing approximately 300 nM bovine Factor IXa, .5 uM bovine Factor X, 100 nM bovine Factor IIa and 10 nM MES buffer at pH 5.6, 0.5% PEG 6000, 1% BSA, and 125 mM NaCl. The cuvettes are then incubated for 1 minute at 37° C. This incubation is followed by an additional of 200 ul of substrate reagent. The substrate reagent is comprised of a water reconstituted lyophilized preparation containing approximately 0.4 mM CH3O-CO-D-CHA-Gly-Arg-pNA N alpha (2-naphthylsulfonylglycyl) -D-L-Amidinophenyl alanine-piperidide (alpha NAPAP) which is a thrombin inhibitor, 15 mM EDTA, 0.250. M NaCl, and 0.020 M Tris at pH 8. A kinetic determination of the reaction in the cuvette is performed immediately after addition of the substrate by recording the change in optical density at 405 nm for one minute.

EXAMPLE 4

Example 1 is repeated, except the reagent to bind von Willebrands Factor (anti-von Willebrands Factor antibody) and the incubation step to eliminate the effects of the von Willebrands Factor are omitted, and the Factor VIII that is added is a mutant Factor VIII which does not bind von Willebrands Factor.

EXAMPLE 5

Example 2 is repeated, except the reagent to bind von Willebrands Factor (anti-von Willebrands Factor antibody) and the incubation step to eliminate the effects of the von Willebrands factor are omitted, and the Factor VIII that is added is a mutant Factor VIII which does not bind von Willebrands Factor.

EXAMPLE 6

Example 3 is repeated, except the reagent to bind von Willebrands factor (anti-von Willebrands Factor antibody) and the incubation step to eliminate the effects of the von Willebrands Factor are omitted, and the Factor VIII that is added is a mutant Factor VIII which does not bind von Willebrands Factor.

What is claimed is:
1. A method for determining levels of free or functional Protein S in a Protein S containing sample the method comprising:
 a. eliminating the effects of von Willebrands Factor;
 b. incubating the sample with activated Protein C, Factor VIII, phospholipids and calcium;
 c. incubating the mixture with factors IIa, IXa, and X;
 d. adding to the incubation mixture a factor Xa specific substrate; and
 e. determining the amount of indicator formed from cleavage of the substrate as a measure of functional Protein S.
2. A method for determining the levels of Protein S in a Protein S containing sample comprising:
 a. combining the Protein S containing sample with (1) a reagent to eliminate the effect of substantially all von Willebrands Factor present in the Protein S containing sample, (2) activated Protein C in an amount sufficient to inactivate a portion of a fixed amount of Factor VIII, (3) phospholipids and (4) calcium ion in amounts sufficient to facilitate the inactivation of Factor VIII;

b. incubating the mixture for a time sufficient to eliminate the effects of the von Willebrands factor;

c. combining the incubation mixture with a fixed amount of Factor VIII;

d. incubating the mixture for a time sufficient to inactivate a portion of the Factor VIII;

e. combining the incubation mixture with Factor IIa, Factor IXa, Factor X and calcium ions whereby there are sufficient amounts of Factor IIa and calcium ion to activate the remaining Factor VIII, and a sufficient amount of Factor IXa to activate the Factor X in the presence of the activated Factor VIII;

f. incubating the mixture until a portion of the Factor X is converted to Factor Xa;

g. adding to the incubation mixture a sufficient amount of thrombin inhibitor to inhibit thrombin activity without affecting Factor Xa activity;

h. adding to the incubation mixture an indicator agent capable of reacting with Factor Xa; and i. measuring the signal molecule.

3. The method of claim 2 wherein the agent to eliminate the effects of the von Willebrands factor on Factor VIII is selected from the group consisting of anti von Willebrands Factor antibody, inactivated Factor VIII which binds to von Willebrands Factor, fragments of Factor VIII that bind to von Willebrands Factor, synthetic peptides that prevent von Willebrands Factor interaction with Factor VIII or enzymes that proteolyze von Willebrands factor so that the resulting proteolysis products do not bind to Factor VIII.

4. The method of claim 2 wherein Factors IIa, VIII, IXa, and X are obtained from an animal source.

5. The method of claim 2 wherein Factors IIa, VIII, IXa, and X are obtained from a recombinant vector propagated in a host cell line.

6. The method of claim 2 wherein Factor VIII is obtained from a recombinant vector propagated in a host cell line so that von Willebrands Factor do not bind the Factor VIII thereby eliminating steps a and b.

7. The method of claim 2 wherein the indicator agent is a chromogenic substance.

8. The method of claim 2 wherein the indicator agent is $CH_{30}CO$-D-CHA-Gly-Arg-pNA.

9. The method of claim 2 wherein the thrombin inhibitor is N alpha (2-Naphthylsulfonylglycyl)-D,L-Amidinophenylalanine piperidide.

10. The method of claim 2 wherein the signal molecule is p-nitroaniline.

11. The method of claim 2 wherein the phospholipid is comprised of between 5 to 40 mole-% phospholipid serine, 0 to 20 mole-% cholesterol and 50 to 90 mole-% of phosphatidyl choline.

12. The method of claim 2 wherein the phospholipid is comprised of 20 mole-% of phosphatidyl serine and 80 mole-% phosphatidyl choline.

13. The method of claim 2 wherein the indicator agent of step (g) additionally contains a quenching composition, the quenching composition being added in an amount sufficient to prevent the conversion of the Factor X to Factor Xa.

14. The method of claim 13 wherein the quenching composition contains ethylenediaminetetraacetic acid.

15. The method of claim 13 with the additional step of adding an acid which disrupts protein mediated reactions to the incubation mixture at a fixed point in time after the addition of the indicator agent.

16. The method of claim 15 wherein the acid is selected from the group consisting of acetic acid and citric acid.

17. The method of claim 2, together with the further step of adding a quenching composition at a fixed point in time after commencement of the reaction converting Factor X to Xa the quenching composition being in an amount sufficient to prevent the conversion of substantially all of Factor X to Factor Xa.

18. The method of claim 17 wherein the quenching substance contains ethylenediaminetetraacetic acid.

19. The method of claim 2 wherein the incubation step (f) is continued until all of Factor X is converted to Factor Xa.

20. A method for determining the levels of Protein S in a Protein S containing sample comprising:

a. combining the Protein S containing sample with (1) a reagent to eliminate the effects of substantially all von Willebrands Factor present in the sample and (2) Protein C in an amount which when activated is sufficient to inactivate a portion of a predetermined amount of Factor VIII and (3) phospholipids and (4) calcium ion in amounts sufficient to facilitate the inactivation of Factor VIII;

b. incubating the mixture for a time sufficient to eliminate the effects of the von Willebrands Factor on Factor VIII;

c. combining the mixture with a sufficient amount of snake venom activator in an amount sufficient to activate the Protein C;

d. incubating the mixture for a time sufficient to activate the Protein C;

e. combining the incubation mixture with a fixed amount of Factor VIII;

f. incubating the mixture for a time sufficient to inactivate a portion of the Factor VIII;

g. combining the incubation mixture with Factor IIa, Factor IXa, Factor X and calcium ions whereby there are sufficient amounts of Factor IIa and calcium ion to activate the remaining Factor VIII, and a sufficient amount of Factor IXa to activate the Factor X in the presence of the activated Factor VIII;

h. Incubating the mixture until a portion of the Factor X is converted to Factor Xa;

i. adding to the incubation mixture whereby to release a signal molecule and a sufficient amount of thrombin inhibitor to inhibit thrombin activity without affecting Factor Xa activity;

j. adding to the incubation mixture an indicator agent capable of reacting with Factor Xa; and k. measuring the signal molecule.

21. A kit for performing a Protein S assay on a sample comprising:

a. a first vessel containing: a sufficient amount of an agent to eliminate the effects on Factor VIII of substantially all of the von Willebrands Factor in the sample and a sufficient amount of Protein C to inactivate a portion of a fixed amount of Factor VIII, and sufficient amount of phospholipid and calcium ion to facilitate the inactivation of the Factor VIII;

b. a second vessel containing: a fixed amount of Factor VIII;

c. a third vessel containing: a sufficient amount of Factor IIa and calcium ion to activate the remaining Factor VIII, and sufficient amounts of Factor X and Factor IXa so as to activate the Factor X to Factor Xa in the presence of the activated Factor VIII;

d. a fourth vessel containing a sufficient quantity of an indicator agent capable of reacting with Factor Xa, and a sufficient amount of a thrombin inhibitor to inhibit thrombin activity without affecting Factor Xa activity.

22. The kit of claim 20 wherein the fourth vessel also contains a quenching composition in an amount sufficient to prevent the conversion of Factor X to Factor Xa.

23. The kit of claim 20 wherein the indicator is selected from the class consisting of: enzymatic, radiometric, fluorescent or chromogenic indicators.

24. The kit of claim 20 wherein the indicator is chromogenic.

25. The kit of claim 20 wherein the indicator is $CH_3OCO$-DCHA-Gly-Arg-pNA.

26. The kit of claim 20 wherein Factors IIa, VIII, IXa, and X are obtained from an animal source.

27. The kit of claim 20 wherein Factors IIa, VIII, IXa, and X are obtained from a recombinant vector propagated in a host cell line.

28. A kit for performing a Protein S assay on a sample comprising:

a. A first vessel containing: a sufficient amount of an agent to eliminate the effects of substantially all of the von Willebrands factor in the sample and a sufficient amount of Protein C to inactivate a portion of a fixed amount of Factor VIII, and sufficient amount of phospholipid and calcium ion to facilitate the inactivation of the Factor VIII;

b. a second vessel containing: a fixed amount of Factor VIII;

c. a third vessel containing: a sufficient amount of Factor IIa and calcium ion to activate the remaining Factor VIII, and sufficient amounts of Factor IXa so as to activate the Factor X to Factor Xa in the presence of the activated Factor VIII;

d. a fourth vessel containing a sufficient quantity of a quenching agent to stop the conversion of Factor X to Factor Xa; and e. a fifth vessel containing a sufficient quantity of an indicator agent capable of reacting with Factor X and a sufficient amount of a thrombin inhibitor to inhibit thrombin activity without affecting Factor Xa activity.

29. The kit of claim 28 wherein the quenching substance contains ethylenediaminetetrraacetic acid.

* * * * *